United States Patent
Mazor et al.

(10) Patent No.: US 6,453,002 B1
(45) Date of Patent: Sep. 17, 2002

(54) DIFFERENTIAL MEASUREMENT OF X-RAY MICROFLUORESCENCE

(75) Inventors: Isaac Mazor, Haifa; Boris Yokhin, Nazareth Illit; David Bar-On, Givat Ella, all of (IL)

(73) Assignee: Jordan Valley Applied Radiation Ltd. (IR)

(*) Notice: Subject to any disclaimer, the term of this patent is extended or adjusted under 35 U.S.C. 154(b) by 0 days.

(21) Appl. No.: 09/551,715

(22) Filed: Apr. 18, 2000

(51) Int. Cl.⁷ .................................................. G01T 1/36
(52) U.S. Cl. .......................................... 378/49; 378/82
(58) Field of Search ............................... 378/49, 44, 45, 378/70, 82, 84, 205; 250/491.1, 492.2

(56) References Cited

U.S. PATENT DOCUMENTS

| | | | |
|---|---|---|---|
| 3,256,431 A | 6/1966 | Fraser | |
| 3,581,087 A | 5/1971 | Brinkerhoff | |
| 3,980,568 A * | 9/1976 | Pitchford et al. | 378/46 |
| 4,085,329 A * | 4/1978 | McCoy et al. | 378/34 |
| 4,710,259 A * | 12/1987 | Howe et al. | 117/15 |
| 4,852,135 A * | 7/1989 | Anisovich et al. | 378/49 |
| 5,497,008 A | 3/1996 | Kumakhov | |
| 5,742,658 A * | 4/1998 | Tiffin et al. | 378/44 |
| 5,778,039 A | 7/1998 | Hossain | |
| 5,937,026 A | 8/1999 | Satoh | |
| 6,173,036 B1 * | 1/2001 | Hossain et al. | 378/45 |
| 6,192,103 B1 * | 2/2001 | Wormington et al. | 378/73 |
| 6,266,389 B1 * | 7/2001 | Murayama et al. | 378/34 |

FOREIGN PATENT DOCUMENTS

JP     09-172047     *  6/1997    ........... H01L/21/66

* cited by examiner

Primary Examiner—Robert H. Kim
Assistant Examiner—Chih-Cheng Kao
(74) Attorney, Agent, or Firm—Hoffman, Wasson & Gitler, PC (57) ABSTRACT

A method of X-ray analysis includes irradiating a spot on a sample with X-rays along an X-ray beam axis. X-rays emitted from the sample, responsive to irradiating the spot, are simultaneously detected at a plurality of different azimuthal angles relative to the beam axis. X-ray intensities detected at the different angles in a common energy range are compared in order to determine a property of the sample.

33 Claims, 4 Drawing Sheets

DIFFERENTIAL MEASUREMENT OF X-RAY MICROFLUORESCENCE

FIELD OF THE INVENTION

The present invention relates generally to X-ray spectrometry, and specifically to methods and devices to detect and analyze X-ray microfluorescence.

BACKGROUND OF THE INVENTION

X-ray microfluorescence analysis is a non-destructive technique known in the art for determining the atomic composition and thickness of thin films. Typically, a focused X-ray beam is directed at a sample, and the X-ray fluorescence induced by the interaction of the X-rays with the sample is detected by a detector located near the sample. The composition and thickness of the irradiated sample are determined from the intensity and energy of the fluorescent X-ray photons.

In "Annular-Type Solid State Detector for a Scanning X-Ray Analytical Microscope," *Review of Scientific Instruments* 66(9) (September, 1995) pp. 4544–4546, which is incorporated herein by reference, Shimomura and Nakazawa describe an annular germanium detector located near an irradiated sample which transduces the energy resulting from X-ray fluorescence into a single channel of data.

U.S. Pat. No. 5,937,026, to Satoh, whose disclosure is incorporated herein by reference, describes a microfluorescent X-ray analyzer in which a capillary tube is used to deliver X-ray excitation to a small region of a sample. The capillary passes through a hole in the center of a flat plate solid-state X-ray detector, which is used to detect fluorescent X-rays emitted by the sample. The geometry of the capillary tube and the detector allows fluorescent X-rays from a small excitation region to be detected over a large solid angle.

U.S. Pat. No. 3,256,431, to Fraser, U.S. Pat. No. 3,581,087, to Brinkerhoff and U.S. Pat. No. 5,778,039, to Hossain, whose disclosures are incorporated herein by reference, describe systems for detection and analysis of X-ray fluorescence using multiple detectors. In all of these patents, a sample is excited by an X-ray source, and the multiple detectors are used to detect the X-ray fluorescence in different, respective energy domains. Typically, the energy domains are chosen to correspond to emission bands of different elements in the sample, so that comparative measurements can be made of the relative concentrations of two elements, for example.

U.S. Pat. No. 5,497,008, to Kumakhov, which is incorporated herein by reference, describes analytic instruments using a polycapillary X-ray optic, also known as a Kumakhov lens, for X-ray fluorescence analysis or spectroscopy. The instruments described use a single fluorescence detector.

SUMMARY OF THE INVENTION

It is an object of some aspects of the present invention to provide improved apparatus and methods for X-ray microfluorescence analysis.

It is a further object of some aspects of the present invention to provide apparatus and methods for detection and analysis of X-ray microfluorescence associated with very small geometrical features of a sample.

It is yet a further object of some aspects of the present invention to provide apparatus and methods for detection of faults occurring in production of semiconductor devices.

In preferred embodiments of the present invention, an X-ray microfluorescence analyzer comprises an X-ray source which irradiates a small spot on a sample, and a plurality of individual detectors arrayed around the spot, so as to capture X-ray photons emitted from the sample responsive to the X-ray illumination. Preferably, the detectors are arrayed in a generally symmetrical pattern about the spot. A processing unit receives signals from the detectors and processes them to compare the intensity of photon emission captured by the different detectors, and thus to detect variations in the intensity as a function of azimuth about the irradiation beam. These variations are indicative of directional inhomogeneity of the emission from the sample.

The detected azimuthal differences in the intensity of emission in a selected energy range are preferably used to determine properties of microscopic structures in the sample under test. Alternatively or additionally, the differences are monitored in order to accurately align the X-ray source and detectors with such structures. The method of the present invention, wherein multiple detectors are used simultaneously to measure emission in a common energy range at different azimuths, is substantively different from methods of X-ray fluorescence analysis known in the art. Such methods, as described in the Background of the Invention, are generally based on detection at only a single azimuth at any given time. When multiple detectors are used, their purpose is to measure emission in different, respective energy ranges, and directional inhomogeneity of emission is not considered.

In some preferred embodiments of the present invention, the analyzer is used to measure overlay errors between successive layers, such as metallization layers, created on a semiconductor wafer in the course of integrated circuit production. Preferably, a test zone is created on the wafer, in which a pattern in a lower layer, using a first element, is overlaid by a substantially identical pattern in an upper layer, using a second, different element. The first and second elements are typically metal elements, although other types of X-ray detectable elements may also be used. When the layers are in proper registration, the pattern in the upper layer substantially shields the element in the lower layer from X-rays and prevents X-ray photons from the first element from reaching the detectors. When there is a registration error, however, a portion of the pattern in the lower layer is exposed to X-rays, so that photons from the first element can reach the detectors. The processing unit analyzes the intensity and direction of emission of these X-ray photons in order to determine the degree and direction of misregistration between the upper and lower layers.

In other preferred embodiments of the present invention, the analyzer is used to determine the composition and thickness of bumps formed on a surface of the sample. Such bumps typically comprise metal bumps, which are formed on the upper surface of a semiconductor wafer, for example, and are then used as contact points between an integrated circuit made from the wafer and a suitable chip carrier (in place of wire bonding). The analyzer of the present invention is used to measure the size and thickness of these bumps, in order to verify that they will provide a suitable connection to the chip carrier. To perform the measurement accurately, however, it is necessary that the small spot that is excited by the X-ray source be accurately aligned with one of the bumps. Preferably, directional inhomogeneity of X-ray emission from the bumps is measured so as to provide an indication of misalignment between the spot and the bump, and thus to drive a translation stage so that the spot and the bump are precisely aligned. Alternatively or additionally, the processing unit averages the signals from the different detectors to compensate for any residual misalignment.

In still other preferred embodiments of the present invention, the sample comprises a crystalline substance, such as single-crystal silicon, which generates a diffraction pattern when irradiated by the X-ray source. The diffraction pattern has directional inhomogeneity, whose direction is determined by an orientation angle of the substance. This diffraction pattern can cause anomalies in measurement of X-ray fluorescence by the analyzer. The processing unit detects the inhomogeneous diffraction pattern by detecting differences in the signals that it receives from the different detectors. Most preferably, the signal differences are used to drive a rotation stage so as to align the sample, relative to the detectors, in a manner that minimizes the impact of the diffraction on the fluorescence measurement. Alternatively, the signal differences may be used to determine the crystal orientation.

There is therefore provided, in accordance with a preferred embodiment of the present invention, a method of X-ray analysis, including:

irradiating a spot on a sample with X-rays along an X-ray beam axis;

simultaneously detecting X-rays emitted from the sample, responsive to irradiating the spot, at a plurality of different azimuthal angles relative to the beam axis; and comparing intensities of the X-rays detected at the different angles in a common energy range in order to determine a property of the sample.

Preferably, irradiating the spot includes irradiating a spot of microscopic size, and comparing the intensities includes determining a geometrical property of a microscopic structure of the sample. Further preferably, simultaneously detecting the X-rays includes detecting X-ray emission using an array of detectors positioned around the spot.

Preferably, comparing the intensities includes detecting an inhomogeneity of the emitted X-rays as a function of azimuth. In a preferred embodiment, detecting the X-rays includes detecting X-rays diffracted from the sample, and detecting the inhomogeneity includes determining an angle of diffraction of the X-rays from a crystalline structure of the sample. Preferably, the method includes introducing a relative rotation between the sample and an array of detectors, responsive to the determined angle, so that the X-rays are diffracted in a desired direction relative to the detectors. Alternatively or additionally, detecting the X-rays further includes detecting fluorescent X-rays emitted by the sample, and comparing the intensities includes using the determined angle to distinguish between the diffracted X-rays and the fluorescent X-rays. Further alternatively or additionally, irradiating the spot includes irradiating a generally symmetrical feature of the sample, and detecting the inhomogeneity includes detecting a misalignment of the spot with the feature.

In a preferred embodiment, detecting the X-rays includes detecting X-rays emitted by a lower feature of the sample, at least a portion of which is covered by an upper feature of the sample so as to block irradiation of the covered portion of the lower feature, and comparing the intensities includes assessing a position of the upper feature relative to the lower feature.

There is also provided, in accordance with a preferred embodiment of the present invention, a method for detecting misregistration of upper and lower layers formed on the surface of a sample, the layers including respective upper and lower features, wherein the upper feature is designed to substantially cover the lower feature, the method including:

irradiating an area of the sample including the upper and lower features with X-rays;

detecting X-rays emitted by the sample in an energy range that is characteristic of the lower feature; and responsive to an intensity of the detected X-rays, assessing an extent to which the lower feature is not covered by the upper feature.

Preferably, detecting the X-rays emitted by the sample includes detecting fluorescent X-rays emitted by a material that is present in the lower feature. Further preferably, the material present in the lower feature includes a first metallic material, and the upper feature includes a second metallic material. Most preferably, the sample includes a semiconductor wafer, and wherein the upper and lower layers include upper and lower metal layers formed on the wafer.

In a preferred embodiment, the method includes forming a test pattern on the wafer, the test pattern including the upper and lower features, which are designed so that when the upper and lower metal layers are properly registered, the upper feature substantially covers the lower feature. Preferably, detecting the X-rays includes detecting X-rays emitted by the sample at a plurality of different azimuthal angles relative to a beam axis of the irradiating X-rays, and assessing the portion of the lower feature that is not covered includes comparing the intensity of the X-rays emitted at the different angles to determine a direction of misregistration of the upper feature with the lower feature.

Preferably, assessing the extent to which the lower feature is not covered by the upper feature includes determining a measure of the area of the lower feature that is not covered by the upper feature.

There is additionally provided, in accordance with a preferred embodiment of the present invention, a method for X-ray analysis of a generally symmetrical feature on the surface of a sample, including:

irradiating the feature with a beam of X-rays having a beam diameter at the surface of the sample that is substantially less than a diameter of the feature;

detecting X-rays emitted from the sample, responsive to irradiating the feature, at a plurality of different azimuthal angles relative to an axis of the irradiating beam; and analyzing a characteristic of the feature responsive to the detected X-rays, using respective intensities of the X-rays detected at the different angles to compensate for a misalignment between the irradiating beam and the feature.

Preferably, detecting the emitted X-rays includes detecting X-ray fluorescence due to an element of the feature, wherein analyzing the characteristic using the respective intensities includes summing the intensities of the X-rays detected at the different angles.

In a preferred embodiment, the feature includes a metal bump formed on the surface of a semiconductor wafer.

Preferably, analyzing the characteristic using the respective intensities includes measuring a difference in the respective intensities of the detected X-rays at opposing azimuths relative to the axis of the irradiating beam. Most preferably, using the respective intensities at the different angles includes relatively shifting the beam and the sample responsive to the measured difference in the intensities, so as to correct the misalignment.

There is further provided, in accordance with a preferred embodiment of the present invention, apparatus for X-ray microanalysis, including:

an X-ray source, adapted to irradiate a spot on a sample with X-rays along an X-ray beam axis;

a plurality of X-ray detectors, arrayed around the spot so as to simultaneously receive X-rays emitted from the sample, responsive to irradiation of the spot, at a plurality of different azimuthal angles relative to the beam axis, and to generate electrical signals responsive to the received X-rays; and a processing unit,-coupled to receive the electrical signals from the detectors and, responsive to the signals, to compare intensities of the X-rays received at the different angles in a common energy range in order to determine a property of the sample.

Preferably, the X-ray source includes X-ray optics, configured to focus the X-ray beam to a spot of microscopic size on the sample. Most preferably, the X-ray optics include a polycapillary array.

There is moreover provided, in accordance with a preferred embodiment of the present invention, apparatus for detecting misregistration of upper and lower layers formed on the surface of a sample, the layers including respective upper and lower features, wherein the upper feature is designed to substantially cover the lower feature, the apparatus including:

an X-ray source, adapted to irradiate an area of the sample including the upper and lower features with X-rays;

a plurality of X-ray detectors, arrayed around the spot so as to simultaneously receive X-rays emitted from the sample in an energy range that is characteristic of the lower feature, and to generate electrical signals responsive to the received X-rays; and a processing unit, coupled to receive the electrical signals from the detectors and responsive to the signals, to assess an extent to which the lower feature is not covered by the upper feature.

There is furthermore provided, in accordance with a preferred embodiment of the present invention, a semiconductor wafer having at least an upper and a lower metal layer deposited thereon, the layers including respective upper and lower features defining a test pattern on the wafer, such that the upper feature substantially shields the lower feature from radiation when the upper and lower metal layers are properly registered with one another, but does not shield at least a portion of the lower feature when the layers are not properly registered.

Preferably, the lower feature includes a first metallic material, and wherein the upper feature includes a second metallic material, the first and second materials having substantially different X-ray fluorescence spectra.

There is additionally provided, in accordance with a preferred embodiment of the present invention, apparatus for X-ray analysis of a generally symmetrical feature on the surface of a sample, including:

an X-ray source, adapted to irradiate the feature with a beam of X-rays having a beam diameter at the surface of the sample that is substantially less than a diameter of the feature;

a plurality of X-ray detectors, arrayed around the spot so as to simultaneously receive X-rays emitted from the sample, responsive to irradiation of the spot, at a plurality of different azimuthal angles relative to an axis of the irradiating beam, and to generate electrical signals responsive to the received X-rays; and a processing unit, coupled to receive the electrical signals from the detectors and, responsive to the signals, to analyze a characteristic of the feature responsive to the detected X-rays, using respective intensities of the X-rays detected at the different angles to compensate for a misalignment between the irradiating beam and the feature.

Preferably, the apparatus includes a translation stage, coupled to be driven by the processing unit so as to shift the sample relative to the detectors, so as to correct the misalignment.

The present invention will be more fully understood from the following detailed description of the preferred embodiments thereof, taken together with the drawings in which:

DETAILED DESCRIPTION OF PREFERRED EMBODIMENTS

Figure 1:
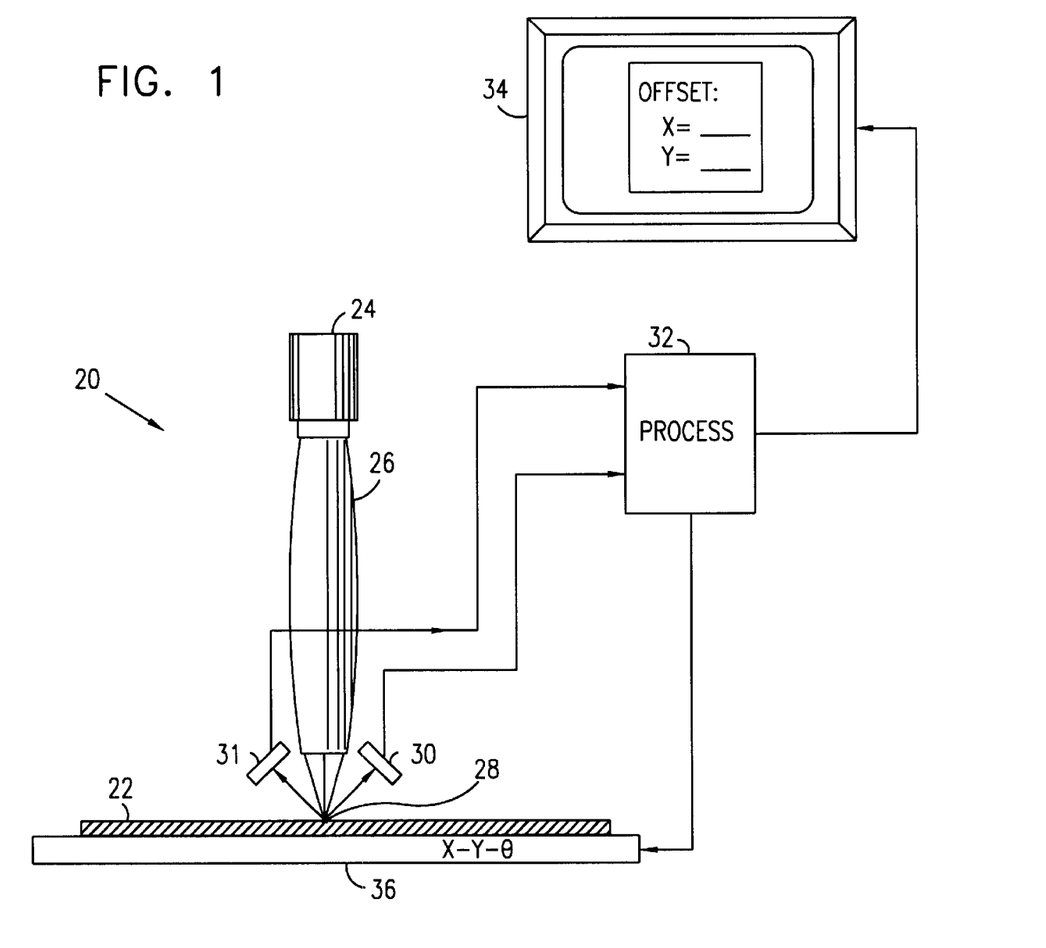
FIG. 1 is a schematic side view of an X-ray microfluorescence analyzer, in accordance with a preferred embodiment of the present invention.

FIG. 1 is a schematic, pictorial illustration of a X-ray microfluorescence analyzer 20, in accordance with a preferred embodiment of the present invention. X-rays emitted by an X-ray source 24 are collected by a focusing optic 26. X-ray source 24 preferably comprises an X-ray tube, such as an XTF 5011 tube produced by Oxford Instruments, Inc., of Scotts Valley, California. Optic 26 is preferably a monolithic polycapillary lens, such as those produced by X-Ray Optical Systems, Inc., of Albany, N.Y. The optic collects the X-rays and focuses them to a spot 28 on a sample 22. In the preferred embodiments described hereinbelow, the sample comprises a silicon wafer, but analyzer 20 may similarly be applied to samples of other types. Most preferably, spot 28 is substantially circular with a diameter of the order of 50 m. Alternatively, optic 26 comprises a monocapillary optic and/or X-ray collimating pinholes, or any other suitable collimating means known in the art.

Fluorescent X-rays, emitted by sample 22 in response to the irradiating X-rays, are produced within spot 28, and are collected by a plurality of detectors 30, 31, 33 and 35 arrayed around the spot. (For clarity of illustration, only detectors 30 and 31 are shown in FIG. 1. All of the detectors appear in FIG. 2.) The arrangement and operation of the detectors are described in more detail hereinbelow. Signals from the detectors are transferred to a processing unit 32, which most preferably comprises a plurality of pulse processors, with a separate input and processing channel for each of the detectors. Each channel determines the spectral intensity of emission captured by the respective detector, preferably using methods of energy-dispersive processing, as are known in the art. An output stage of processing unit 32 analyzes sums and differences of the signals from the different detectors in order to measure the spectral intensity of X-ray emission from the sample and azimuthal variations in the intensity. These measurements are used determine the local structure and composition of sample 22 at spot 28, as described hereinbelow. The resultant information is then output to a display 34.

Preferably sample 22 is scanned by a translation/rotation stage 36, as is known in the art, under the control of processing unit 32. Stage 36 is used to align spot 28 and the array of detectors with features of interest in the sample and to allow different areas of the sample to be tested. Alternatively the X-ray tube, optics and detectors are together scanned over the sample.

Figure 2:
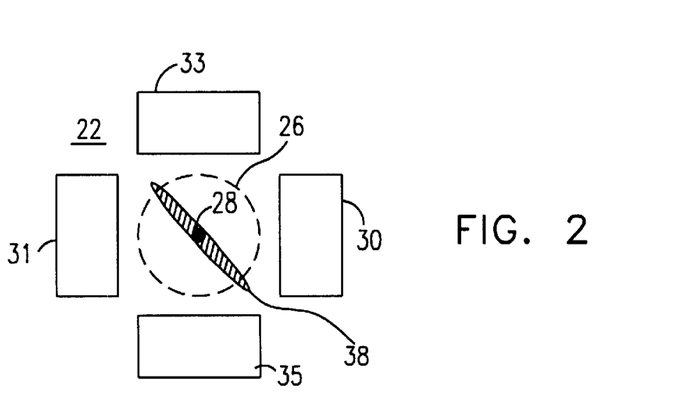
FIG. 2 is a schematic top view of a detail of the analyzer of FIG. 1, in accordance with a preferred embodiment of the present invention.

FIG. 2 is a schematic top view of spot 28 formed on sample 22 and of detectors 30, 31, 33 and 35 positioned around the spot, in accordance with a preferred embodiment of the present invention. Preferably, the detectors comprise four PIN diodes, such as type S1223 PIN diodes produced by Hamamatsu Photonics, K. K., of Hamamatsu City, Japan. The detectors are arranged symmetrically about spot 28 and are preferably positioned as close as is practically possible to the spot. Thus, in the present embodiment, in which each of the detectors has an active collection area in the form of a square of side 2.5 mm, the detectors are arranged in a square having sides of approximately 9 mm and at a distance of approximately 4 mm from the surface of sample 22. Preferably, as shown in FIG. 1, the detectors are angled towards spot 28, in order to increase the active area presented to the spot. It will be appreciated that the number and type of detectors and their dimensions and positions are described herein by way of example, and other numbers, sizes, positions and types of detectors may similarly be used. For example, another analyzer of this general type is described in U.S. patent application Ser. No. 09/114,789, which is assigned to the assignee of the present patent application, and whose disclosure is incorporated herein by reference.

During irradiation by source 24, spot 28 generates fluorescent X-ray photons which are incident on the detectors, wherein corresponding pulses are in turn generated in the detectors and conveyed to processing unit 32. The processing unit analyzes and counts the pulses from the plurality of detectors. Most preferably, spot 28 and detectors 30, 31, 33 and 35 are maintained substantially stationary in relation to sample 22 until sufficient counts have been recorded by unit 32 in one or more spectral regions of interest for a satisfactory measurement to be made. Processing unit 32 then moves sample 22 using stage 36 to a new spot to be analyzed.

When sample 22 comprises a crystalline substance, such as a semiconductor wafer, X-rays incident at spot 28 are diffracted in a characteristic diffraction pattern. This pattern is illustrated schematically by a shaded pattern 38 on sample 22. Some of the diffracted X-rays reach the detectors and can cause saturation of the detectors or pulse pile-up in unit 32, or can otherwise confuse measurements of X-ray fluorescence (XRF) by the detectors. Such interference by diffracted radiation in XRF measurements is known in the art. The accepted solution is to rotate the sample until, by trial and error, the effect of diffracted radiation on the XRF measurement is minimized.

FIG. 2 illustrates a superior solution to this problem that is made possible by the present invention. Processing unit 32 measures the azimuthal inhomogeneity of the X-ray signals that are received from spot 28, preferably by comparing a sum of the signals from detectors 30 and 31 to a sum of the signals from detectors 33 and 35. In the orientation shown in FIG. 2, in which pattern 38 falls along a diagonal of the square defined by the detectors, the two sums will be approximately identical. The interference of the diffracted radiation with the XRF measurement will be minimized in this orientation. Thus, to cancel the effect of the diffraction, unit 32 preferably rotates stage 36 until the sums are equalized. Alternatively or additionally, the initial difference between the sum of the signals from detectors 30 and 31 and that from detectors 33 and 35 is computed by the processing unit and is then used to calculate an optimal angle to which stage 36 should be rotated in order to minimize the diffraction effect.

Figure 3:
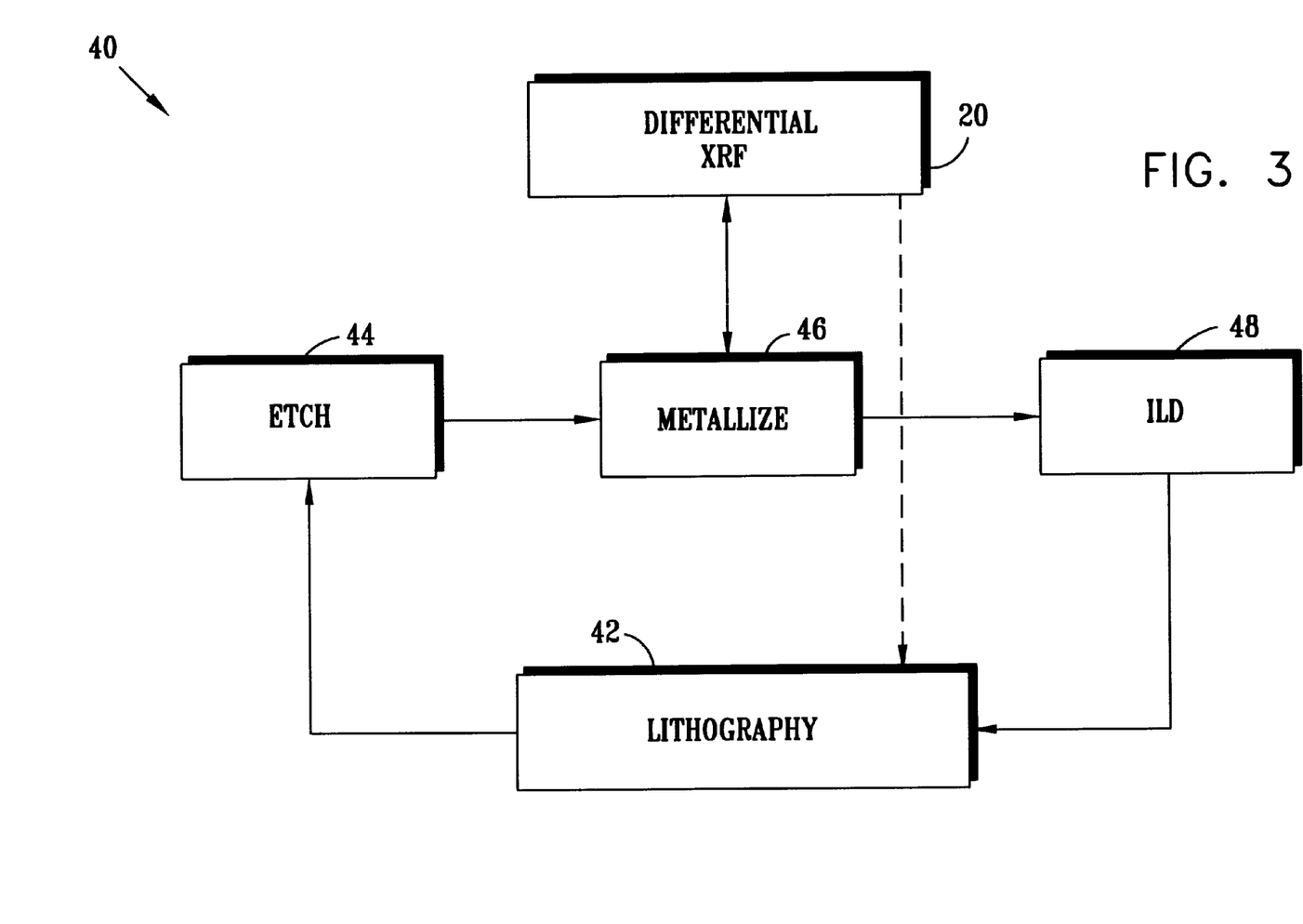
FIG. 3 is a block diagram that schematically illustrates an application of an X-ray microfluorescence analyzer in a semiconductor production process, in accordance with a preferred embodiment of the present invention.

FIG. 3 is a block diagram that schematically illustrates a system 40 for processing of semiconductor wafers using analyzer 20, in accordance with a preferred embodiment of the present invention. In this system, differential XRF analysis is used to verify that microscopic features formed on the wafer have the proper shape, composition and mutual registration. Analyzer 20 is preferably integrated on-line with the processing of the wafer, so that as successive layers are formed on the wafer, each new layer can be tested and verified in turn. System 40 is shown here by way of example, and integration of analyzer 20 into other types of processing systems will be clear to those skilled in the art.

For each layer to be formed on the wafer, a microlithographic stepper 42 forms a mask pattern on photoresist that is deposited on the wafer surface, as is known in the art. The photoresist is developed and etched by an etcher 44, and a metal layer is filled into channels created by the etching, in a metallization chamber 46. Alternatively, the order of the steps may be reversed, so that the metal layer is applied to the entire wafer surface, followed by patterning and etching of the metal. In either case, analyzer 20 measures differential XRF signals generated by the metal elements in the metal layers, as described hereinbelow. Alternatively, XRF signals due to non-metal elements may be detected and analyzed in like manner. When any deviation is discovered in these differential measurements, the result is used to adjust system 40 so as to correct the deviation on the next wafer to be processed. For example, as illustrated in FIG. 3, stepper 42 is adjusted to correct for misregistration of successive metal layers detected by analyzer 20. After metallization, an interlayer dielectric is deposited over the surface of the wafer in a dielectric deposition chamber 48.

Figure 4:
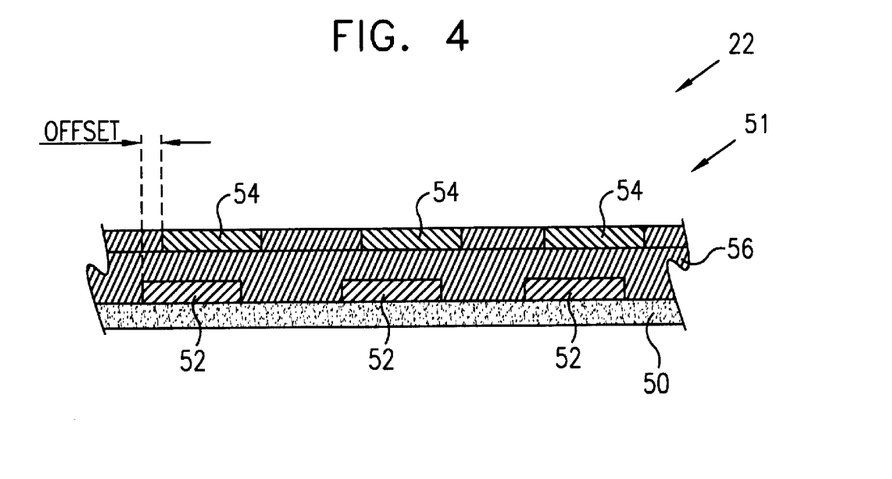
FIG. 4 is a schematic, sectional illustration of a metallization test pattern formed on a semiconductor wafer, in accordance with a preferred embodiment of the present invention.
Figure 5:
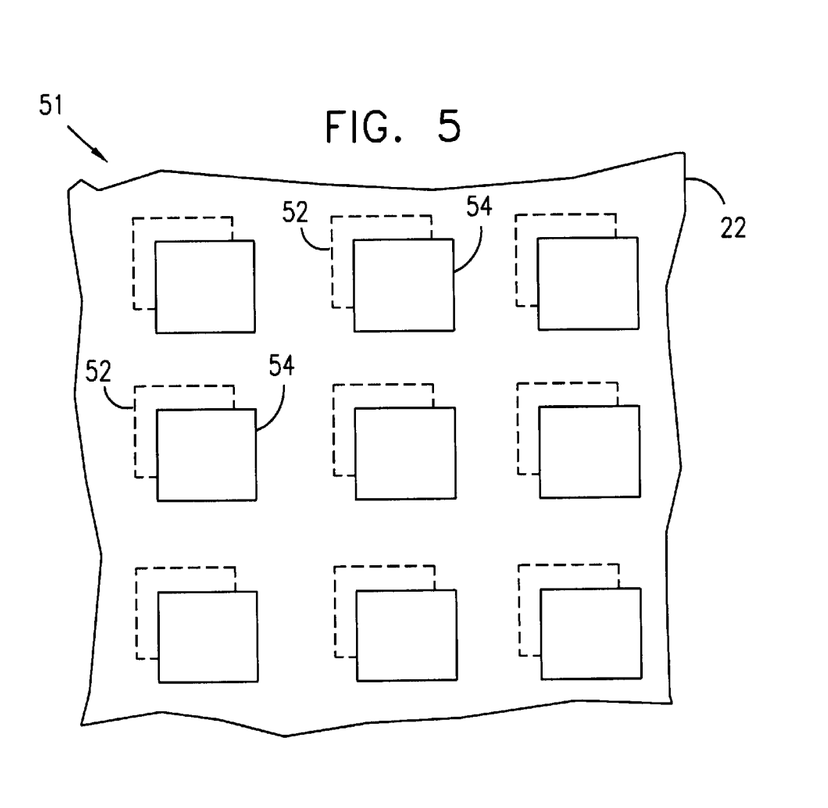
FIG. 5 is a schematic top view of the pattern of FIG. 4.

FIGS. 4 and 5 schematically illustrate a metallization pattern 51 formed on wafer 22 for the purpose of testing the mutual registration of successive metal layers, in accordance with a preferred embodiment of the present invention. FIG. 4 is a sectional view, while FIG. 5 is a top view of the wafer. The pattern comprises a lower grid of pads 52 of a first metal, say tungsten, which is overlaid by an upper grid of pads 54 of a second metal, say aluminum or copper. The two grids are preferably formed in the course of processing wafer 22 in system 40 and have a pitch on the order of the pitch of functional circuit features that are formed on the wafer. Preferably, the pattern is included in lithographic masks that are written onto the wafer by stepper 42 during successive photolithography cycles. In this manner, pads 52 are deposited onto a lower dielectric level 50 as part of a lower metal layer, after which pads 54 are deposited onto an upper dielectric layer 56 as part of an upper metal layer.

The masks are designed so that when the upper and lower metal layers are perfectly registered with one another, each of pads 52 is fully covered by a respective one of pads 54. When there is a misregistration of the metal layers, however, there will be an offset of the upper and lower grids, as shown in the figures. Similarly, if there is a discrepancy in the dimensions of the upper and lower pads, due to inaccurate control of etching parameters, for example, pads 54 may not cover the respective pads 52 completely. Thus, the mutual registration of pads 52 and 54 is indicative of the registration of the functional metal layers deposited on wafer 22.

Because metal pads 54 are relatively opaque to X-rays, the portion of pads 52 that are directly below corresponding pads 54 receive relatively little irradiation from source 24. Furthermore, most of the X-ray fluorescence emitted from this covered portion of the lower pads will be absorbed by the corresponding upper pads. Therefore, when the upper and lower metal layers are perfectly registered, and pattern 51 is irradiated by source 24, the number of fluorescent photons received by detectors 30, 31, 33 and 35 in the characteristic emission bands of the first metal (from which pads 52 are formed) will generally be small. Furthermore, the signals received by each pair of opposing detectors (30 vs. 31, and 33 vs. 35) will be substantially symmetrical.

On the other hand, when there is an offset between the metal layers, as shown in FIGS. 4 and 5, a portion of pads 52 is exposed to irradiation and contributes photons to the flux received by the detectors. The total magnitude of this flux gives a measure of the extent of misregistration between the metal layers. A reference flux level can be determined based on the detector signals measured in a characteristic emission band of the second metal, from which upper pads 54 are formed. Even small errors in registration of the upper and lower pads, on the order of 1%, can be detected in this manner, so that corrective action can be taken before the errors become critical.

Furthermore, when the misregistration is relatively small, the direction and magnitude of the misregistration offset can be determined based on the difference between the fluorescence signals received from opposing detectors in the emission band of the first (lower) metal. Left-right misregistration (in the perspective of FIG. 2) is thus given by the difference in signals between detectors 30 and 31, while up-down misregistration is given by the difference between detectors 33 and 35. The differences between the signals are preferably normalized by a sum of the signals. Analyzer 20 thus provides feedback to stepper 42 (or to an operator of the stepper) indicating not only that a registration error has occurred, but also giving an estimate of the amount and direction of adjustment that are needed in order to prevent the error from occurring in subsequent wafers.

Figure 6:
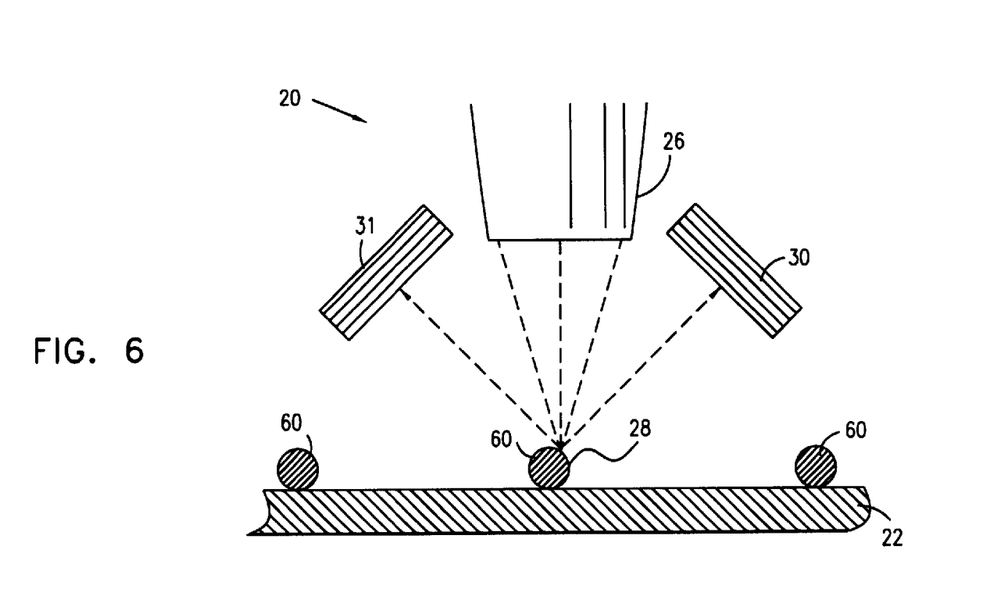
FIG. 6 is a schematic, sectional view of a detail of the analyzer of FIG. 1, applied to analyze bumps on the surface of a sample, in accordance with a preferred embodiment of the present invention.

FIG. 6 is a schematic, sectional view of a detail of wafer 22 under test in analyzer 20, in accordance with another preferred embodiment of the present invention. In this embodiment, metal bumps 60 have been formed on an upper surface of the wafer. These bumps, typically about 0.1 mm across, are used for soldering microelectronic devices that are made from wafer 22 onto suitable chip carriers, in place of wire bonding. Analyzer 20 is used to ascertain that the composition and thickness of bumps 60 meet design parameters.

When only a single X-ray detector is used to capture fluorescent photons emitted from bumps 60, as in XRF microanalyzers known in the art, the measurement of fluorescence intensity will be prone to error due to inaccurate alignment of spot 28 with bump 60. The error arises from variations that occur in XRF emission as a function of the radiation angle relative to the surface of the bump. This difficulty is overcome by differential measurement using analyzer 20. Preferably, differences between the XRF signals received from detectors 30, 31, 33 and 35 are measured in order to determine how far off spot 28 is from the center of bump 60. When the spot is perfectly centered, all of the detectors will give substantially equal signals. The differences between the signals are preferably provided as a negative feedback input to stage 36, so as to drive the bump into alignment with the irradiation spot. Alternatively or additionally, reliable XRF measurements can be made even when the spot is not perfectly aligned on the bump, by taking a sum or average of the signals received from the detectors.

Although the preferred embodiments described herein deal specifically with measurements made on certain specific features of wafer 22, the principles of the present invention may be applied in a straightforward manner to measurement of other microscopic geometrical features on or near a surface of a semiconductor wafer. Furthermore, these principles may similarly be applied to the analysis of other types of microscopic features and structures, in samples other than semiconductor wafers, and to the control of production processes for making such features and structures. For example, the principles described above with reference to FIG. 6 may be applied in other contexts in which X-ray emissions are measured from a curved surface. The ratios of the signals received by the opposing detectors are indicative of the slope of the surface at the point of measurement. The location of the point of measurement may be adjusted, based on the ratios, to find a point of horizontal slope, as in the method of FIG. 6, or to find another predefined slope.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method of X-ray analysis, comprising:
   irradiating a spot on a sample with X-rays along an X-ray beam axis;
   simultaneously detecting X-rays emitted from the sample, responsive to irradiating the spot, at a plurality of different azimuthal angles relative to the beam axis; and
   comparing intensities of the X-rays detected at the different angles in a common energy range in order to determine a property of the sample,
   wherein comparing the intensities comprises detecting an inhomogeneity of the emitted X-rays as a function of azimuth.

2. A method according to claim 1, wherein irradiating the spot comprises irradiating a spot of microscopic size, and wherein comparing the intensities comprises determining a geometrical property of a microscopic structure of the sample.

3. A method according to claim 1, wherein simultaneously detecting the X-rays comprises detecting X-ray emission using an array of detectors positioned around the spot.

4. A method according to claim 1, wherein detecting the X-rays comprises detecting X-rays diffracted from the sample, and wherein detecting the inhomogeneity comprises determining an angle of diffraction of the X-rays from a crystalline structure of the sample.

5. A method according to claim 4, and comprising introducing a relative rotation between the sample and an array of detectors, responsive to the determined angle, so that the X-rays are diffracted in a desired direction relative to the detectors.

6. A method according to claim 4, wherein detecting the X-rays further comprises detecting fluorescent X-rays emitted by the sample, and wherein comparing the intensities comprises using the determined angle to distinguish between the diffracted X-rays and the fluorescent X-rays.

7. A method according to claim 1, wherein irradiating the spot comprises irradiating a generally symmetrical feature of the sample, and wherein detecting the inhomogeneity comprises detecting a misalignment of the spot with the feature.

8. A method of X-ray analysis, comprising:
   irradiating a spot on a sample with X-rays along an X-ray beam axis;
   simultaneously detecting X-rays emitted from the sample, responsive to irradiating the spot, at a plurality of different azimuthal angles relative to the beam axis; and
   comparing intensities of the X-rays detected at the different angles in a common energy range in order to determine a property of the sample,
   wherein detecting the X-rays comprises detecting X-rays emitted by a lower feature of the sample, at least a portion of which is covered by an upper feature of the sample so as to block irradiation of the covered portion of the lower feature, and wherein comparing the intensities comprises assessing a position of the upper feature relative to the lower feature.

9. A method for detecting misregistration of upper and lower metallic layers formed on the surface of a semiconductor wafer, the layers including respective upper and lower features, wherein the upper feature is designed to substantially cover the lower feature, the method comprising:
   irradiating an area of the semiconductor wafer including the respective upper and lower features of the upper and lower metallic layers with X-rays;
   detecting X-rays emitted by the semiconductor wafer in an energy range that is characteristic of the lower feature; and
   responsive to an intensity of the detected X-rays, assessing alignment of the metallic layers.

10. A method according to claim 9, wherein detecting the X-rays emitted by the sample comprises detecting fluorescent X-rays emitted by a material that is present in the lower feature.

11. A method according to claim 10, wherein the material present in the lower feature comprises a first metallic material, and wherein the upper feature comprises a second metallic material.

12. A method according to claim 9, and comprising forming a test pattern on the wafer, the test pattern comprising the upper and lower features, which are designed so that when the upper and lower metal layers are properly registered, the upper feature substantially covers the lower feature.

13. A method according to claim 12, wherein detecting the X-rays comprises detecting X-rays emitted by the sample at a plurality of different azimuthal angles relative to a beam axis of the irradiating X-rays, and wherein assessing the portion of the lower feature that is not covered comprises comparing the intensity of the X-rays emitted at the different angles to determine a direction of misregistration of the upper feature with the lower feature.

14. A method according to claim 9, wherein assessing the extent to which the lower feature is not covered by the upper feature comprises determining a measure of the area of the lower feature that is not covered by the upper feature.

15. A method for X-ray analysis of a generally symmetrical feature on the surface of a sample, comprising:
   irradiating the feature with a beam of X-rays having a beam diameter at the surface of the sample that is substantially less than a diameter of the feature;
   detecting X-rays emitted from the sample, responsive to irradiating the feature, at a plurality of different azimuthal angles relative to an axis of the irradiating beam; and
   analyzing a characteristic of the feature responsive to the detected X-rays, using respective intensities of the X-rays detected at the different angles to compensate for a misalignment between the irradiating beam and the feature.

16. A method according to claim 15, wherein detecting the emitted X-rays comprises detecting X-ray fluorescence due to an element of the feature.

17. A method according to claim 16, wherein analyzing the characteristic using the respective intensities comprises summing the intensities of,the X-rays detected at the different angles.

18. A method according to claim 15, wherein the feature comprises a metal bump formed on the surface of a semiconductor wafer.

19. A method according to claim 13, wherein analyzing the characteristic using the respective intensities comprises measuring a difference in the respective intensities of the detected X-rays at opposing azimuths relative to the axis of the irradiating beam.

20. A method according to claim 19, wherein using the respective intensities at the different angles comprises relatively shifting the beam and the sample responsive to the measured difference in the intensities, so as to correct the misalignment.

21. Apparatus for X-ray microanalysis, comprising:
   an X-ray source, adapted to irradiate a spot on a sample with X-rays along an X-ray beam axis;
   a plurality of X-ray detectors, arrayed around the spot so as to simultaneously receive X-rays emitted from the sample, responsive to irradiation of the spot, at a plurality of different azimuthal angles relative to the beam axis, and to generate electrical signals responsive to the received X-rays; and
   a processing unit, coupled to receive the electrical signals from the detectors and, responsive to the signals, to compare intensities of the X-rays received at the different angles in a common energy range in order to detect an inhomogeneity of the emitted X-rays as a function of azimuth, thereby to determine a property of the sample.

22. Apparatus according to claim 21, wherein the X-ray source comprises X-ray optics, operative to focus the X-ray beam to a spot of microscopic size on the sample.

23. Apparatus according to claim 22, wherein the X-ray optics comprise a polycapillary array.

24. Apparatus according to claim 21, wherein the X-rays emitted from the sample comprise X-rays diffracted from a crystalline structure of the sample at a given diffraction angle, and wherein the processing unit is adapted, responsive to the signals received from the detectors, to determine the angle of diffraction.

25. Apparatus according to claim 24, and comprising a rotation stage, which is coupled to be driven by the processing. unit so as to orient the detectors in a desired orientation relative to the angle of diffraction.

26. Apparatus according to claim 24, wherein the X-rays emitted from the sample and received by the detectors further comprise fluorescent X-rays emitted by the sample.

27. Apparatus for detecting misregistration of upper and lower metallic layers formed on the surface of a semiconductor wafer, the layers including respective upper and lower features, wherein the upper feature is designed to substantially cover the lower feature, the apparatus comprising:

an X-ray source, adapted to irradiate an area of the semiconductor wafer including the upper and lower features of the upper and lower metallic layers with X-rays;

a plurality of X-ray detectors, arrayed around the spot so as to simultaneously receive X-rays emitted from the semiconductor wafer in an energy range that is characteristic of the lower feature, and to generate electrical signals responsive to the received X-rays; and a processing unit, coupled to receive the electrical signals from the detectors and responsive to the signals, to assess alignment of the metallic layers.

28. Apparatus according to claim 27, wherein the X-ray detectors receive fluorescent X-rays emitted by a material that is present in the lower feature.

29. Apparatus according to claim 27, wherein the plurality of X-ray detectors are positioned so as to detect X-rays emitted by the sample at a plurality of different azimuthal angles relative to a beam axis of the irradiating X-rays, and wherein the processing unit is adapted to compare the intensities of the X-rays emitted at the different angles in order to determine a direction of misregistration of the upper feature with the lower feature.

30. Apparatus for X-ray analysis of a generally symmetrical feature on the surface of a sample, comprising:

an X-ray source, adapted to irradiate the feature with a beam of X-rays having a beam diameter at the surface of the sample that is substantially less than a diameter of the feature;

a plurality of X-ray detectors, arrayed around the spot so as to simultaneously receive X-rays emitted from the sample, responsive to irradiation of the spot, at a plurality of different azimuthal angles relative to an axis of the irradiating beam, and to generate electrical signals responsive to the received X-rays; and a processing unit, coupled to receive the electrical signals from the detectors and, responsive to the signals, to analyze a characteristic of the feature responsive to the detected X-rays, using respective intensities of the X-rays detected at the different angles to compensate for a misalignment between the irradiating beam and the feature.

31. Apparatus according to claim 30, wherein the emitted X-rays comprise X-ray fluorescence emitted by an element of the feature.

32. Apparatus according to claim 30, wherein the sample comprises a semiconductor wafer, and wherein the feature comprises a metal bump formed on the surface of the wafer.

33. Apparatus according to claim 30, and comprising a translation stage, coupled to be driven by the processing unit so as to shift the sample relative to the detectors, so as to correct the misalignment.

* * * * *